(12) United States Patent
Takemoto

(10) Patent No.: US 8,550,984 B2
(45) Date of Patent: Oct. 8, 2013

(54) INSERTION AUXILIARY IMPLEMENT

(75) Inventor: Shotaro Takemoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 1184 days.

(21) Appl. No.: 10/997,028

(22) Filed: Nov. 24, 2004

(65) Prior Publication Data

US 2005/0119525 A1  Jun. 2, 2005

(30) Foreign Application Priority Data

Nov. 27, 2003  (JP) ................................ 2003-397377

(51) Int. Cl.
*A61B 1/00* (2006.01)
*A61B 1/04* (2006.01)
*A61M 5/178* (2006.01)

(52) U.S. Cl.
USPC ...... 600/114; 600/104; 600/125; 604/167.02; 604/167.06

(58) Field of Classification Search
USPC ......... 600/114, 129, 130, 194, 121, 201, 104, 600/113, 120–124, 154, 159, 204, 125, 153, 600/155, 156, 157, 158; 604/164.11, 604/165.02, 167.06
See application file for complete search history.

(56) References Cited

U.S. PATENT DOCUMENTS

| | | | | |
|---|---|---|---|---|
| 5,279,610 A | * | 1/1994 | Park et al. | 606/108 |
| 5,540,648 A | * | 7/1996 | Yoon | 600/114 |
| 5,846,182 A | | 12/1998 | Wolcott | |
| 6,022,313 A | * | 2/2000 | Ginn et al. | 600/114 |
| 6,071,233 A | * | 6/2000 | Ishikawa et al. | 600/104 |
| 6,117,070 A | * | 9/2000 | Akiba | 600/154 |
| 6,126,643 A | * | 10/2000 | Vaillancouert | 604/218 |
| 6,328,730 B1 | * | 12/2001 | Harkrider, Jr. | 600/130 |
| 6,458,077 B1 | * | 10/2002 | Boebel et al. | 600/114 |
| 6,517,549 B1 | | 2/2003 | Dennis | |
| 6,676,637 B1 | * | 1/2004 | Bonnette et al. | 604/165.02 |
| 6,786,864 B2 | * | 9/2004 | Matsuura et al. | 600/104 |

(Continued)

FOREIGN PATENT DOCUMENTS

| | | |
|---|---|---|
| JP | H02-23502 | 2/1990 |
| JP | H03-054603 | 5/1991 |

(Continued)

OTHER PUBLICATIONS

Japanese Office Action dated Jun. 29, 2010 with English translation.

(Continued)

*Primary Examiner* — Alireza Nia
(74) *Attorney, Agent, or Firm* — Scully, Scott, Murphy & Presser, P.C.

(57) ABSTRACT

An insertion auxiliary implement of the present invention includes: a tubular part into which a flexible endoscope insertion part which is insertable into a body cavity, and one of a treatment tool and a channel into which the treatment tool is insertable, are insertable; and a sealing member which has through holes for supporting the endoscope insertion part and one of the treatment tool and the channel in the tubular part, and which airtightly and movably contacts each of a periphery of the endoscope insertion part, a periphery of the treatment tool or a periphery of the channel, and an inner surface of the tubular part, and thereby maintains airtightness between a distal end and a proximal end inside the tubular part.

9 Claims, 13 Drawing Sheets

(56) References Cited

U.S. PATENT DOCUMENTS

| | | | |
|---|---|---|---|
| 6,849,043 B2 * | 2/2005 | Kondo | 600/159 |
| 6,929,620 B2 * | 8/2005 | Hasegawa | 604/82 |
| 6,997,931 B2 * | 2/2006 | Sauer et al. | 600/104 |
| 7,036,509 B2 * | 5/2006 | Rapacki et al. | 128/207.14 |
| 7,485,092 B1 * | 2/2009 | Stewart et al. | 600/127 |
| 7,699,861 B2 * | 4/2010 | Bayer | 606/159 |
| 2002/0107530 A1 * | 8/2002 | Sauer et al. | 606/139 |
| 2003/0009194 A1 * | 1/2003 | Saker et al. | 606/213 |
| 2003/0135091 A1 | 7/2003 | Nakazawa et al. | |
| 2004/0073088 A1 * | 4/2004 | Friedman et al. | 600/114 |

FOREIGN PATENT DOCUMENTS

| | | |
|---|---|---|
| JP | H03-231622 | 10/1991 |
| JP | 7-163516 | 6/1995 |
| JP | H07-039847 | 7/1995 |
| JP | 10-146315 | 6/1998 |
| JP | 2001-292959 | 10/2001 |
| JP | 2003-204920 | 7/2003 |

OTHER PUBLICATIONS

Japanese Office Action (Notice of Allowance) dated Sep. 14, 2010.
Japanese Office Action dated Sep. 8, 2009 with Translation.

* cited by examiner

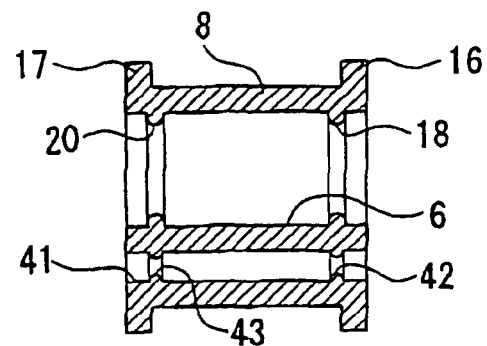
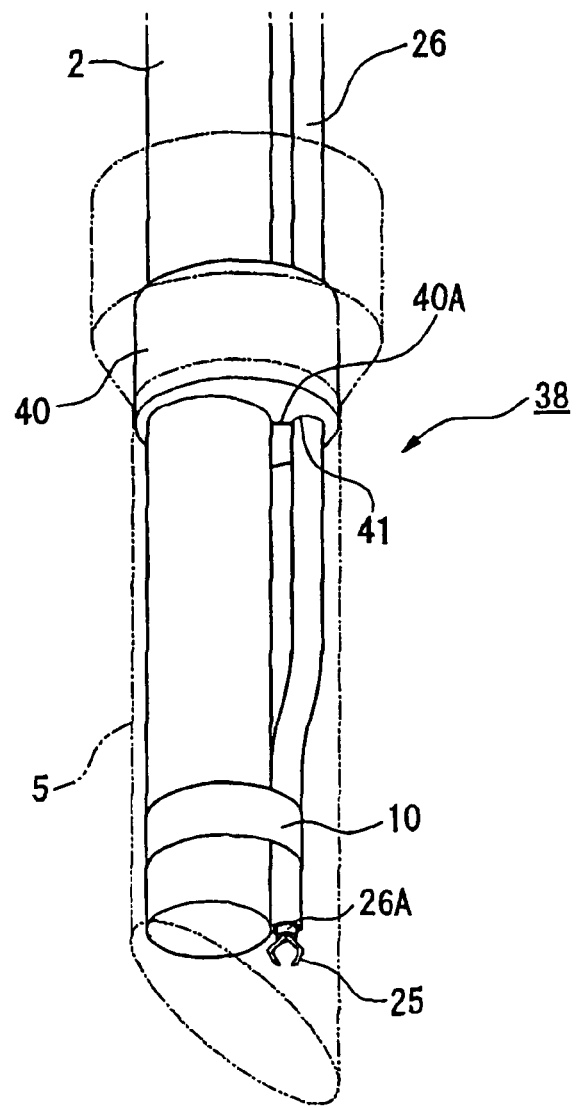

INSERTION AUXILIARY IMPLEMENT

BACKGROUND OF THE INVENTION

Priority is claimed on Japanese Patent Application No. 2003-397377, filed Nov. 27, 2003, the contents of which are incorporated herein by reference.

FIELD OF THE INVENTION

The present invention relates to an insertion auxiliary implement which is used for inserting an endoscope, etc., into a body cavity.

DESCRIPTION OF RELATED ART

Endoscopes are widely used for purposes of diagnosis and treatment of tumors in the stomach, esophagus, etc., and diseases in the alimentary canal such as varicose veins. However, when inserting an endoscope insertion part, for example, into the esophagus via the mouth, an operator is required to be skilled in order to insert it with less pain for the patient. Furthermore, depending on the operations, there are cases in which the endoscope is inserted and extracted repeatedly, and in such a case, the discomfort to the patient becomes larger.

Therefore, a tubular shaped insertion auxiliary implement is proposed in order to easily insert the endoscope insertion part into the esophagus by securing an insertion passage for the endoscope insertion part (for example, refer to FIG. 1 of Japanese Unexamined Patent Application, First Publication No. H07-163516).

SUMMARY OF THE INVENTION

An insertion auxiliary implement of the present invention includes: a tubular part into which a flexible endoscope insertion part which is insertable into a body cavity, and one of a treatment tool and a channel into which the treatment tool is insertable, are insertable; and a sealing member which has through holes for supporting the endoscope insertion part and one of the treatment tool and the channel in the tubular part, and which airtightly and movably contacts each of a periphery of the endoscope insertion part, a periphery of the treatment tool or a periphery of the channel, and an inner surface of the tubular part, and thereby maintains airtightness between a distal end and a proximal end inside the tubular part.

Another insertion auxiliary implement of the present invention includes: a tubular part into which a flexible endoscope insertion part which is insertable into a body cavity, and one of a treatment tool and a channel into which the treatment tool is insertable, are insertable; and a sealing member which has through holes for supporting the endoscope insertion part and one of the treatment tool and the channel in the tubular part, and which is fixed to at least one of a periphery of the endoscope insertion part, a periphery of the treatment tool or a periphery of the channel, and an inner surface of the tubular part, and which is airtightly and movably contacted with others, and thereby maintains airtightness between a distal end and a proximal end inside the tubular part.

The sealing member may include at least one of: a first slide portion which airtightly and slidably contacts the inner surface of the tubular part; a second slide portion which airtightly and slidably contacts the periphery of the endoscope insertion part; and a third slide portion which airtightly and slidably contacts the periphery of the treatment tool or the periphery of the channel.

The insertion auxiliary implement may satisfy at least one of the following: the first slide portion is a convexity which contacts the inner surface of the tubular part; the second slide portion is a convexity which contacts the periphery of the endoscope insertion part; and the third slide portion is a convexity which contacts the periphery of the treatment tool or the periphery of the channel.

A reinforcing band may be provided which wraps around the sealing member so that an outer portion of the sealing member, which is away from the inner surface of the tubular part, is covered.

A fastener which fastens the endoscope insertion part, and one of the treatment tool and the channel together, may be provided.

The channel in which the treatment tool is inserted may be inserted in the through hole of the sealing member, and a sealing structure may be provided between the inner surface of the channel and the periphery of the treatment tool.

The sealing member may include a first slide portion which airtightly and slidably contacts the inner surface of the tubular part, at at least two locations along the axial direction of the tubular part.

The sealing member may include a second slide portion which airtightly and slidably contacts the periphery of the endoscope insertion part, at at least two locations along the axial direction of the tubular part.

The sealing member may include a third slide portion which airtightly and slidably contacts the periphery of the treatment tool or the periphery of the channel, at at least two locations along the axial direction of the tubular part.

The reinforcing band may be non-contacting with the inner surface of the tubular part when the sealing member is inserted in the tubular part.

In the case in which the first slide portion is a convexity which contacts the inner surface of the tubular part, the convexity may have elasticity and external dimensions larger than internal dimensions of the tubular part.

In the case in which the second slide portion is a convexity which contacts the periphery of the endoscope insertion part, the convexity may have elasticity and internal dimensions smaller than external dimensions of the periphery of the endoscope insertion part.

In the case in which the third slide portion is a convexity which contacts the periphery of the treatment tool or the periphery of the channel, the convexity may have elasticity and internal dimensions smaller than external dimensions of the periphery of the treatment tool or the periphery of the channel.

BRIEF DESCRIPTION OF THE DRAWINGS

FIG. 13 is a cross sectional view of the sealing member of an insertion auxiliary implement according to a second embodiment of the present invention, when it is seen in a section including its axis.

FIG. 14 is a perspective view of the insertion auxiliary implement.

DETAILED DESCRIPTION OF THE INVENTION

A first embodiment according to the present invention will be explained below with reference to FIGS. 1 to 12.

Figure 1:
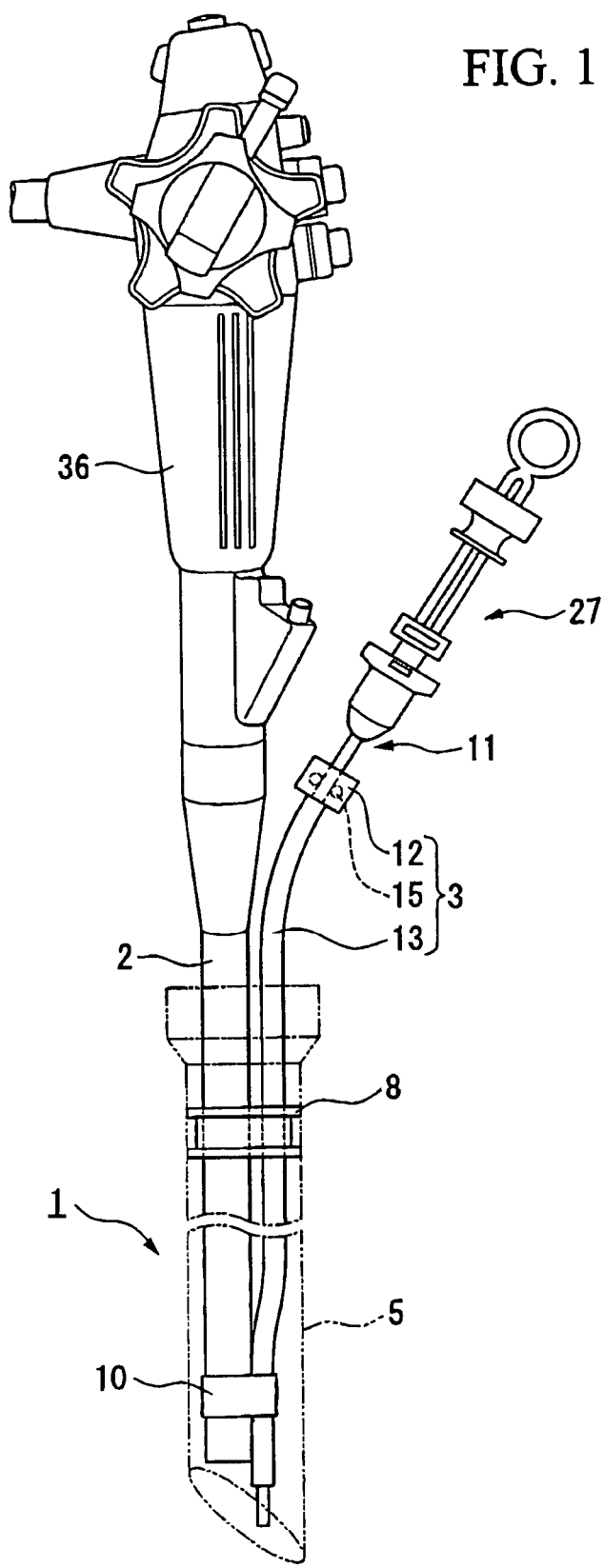
FIG. 1 is a side view of an insertion auxiliary implement according to a first embodiment of the present invention, an endoscope insertion part, and a ligation apparatus.
Figure 2:
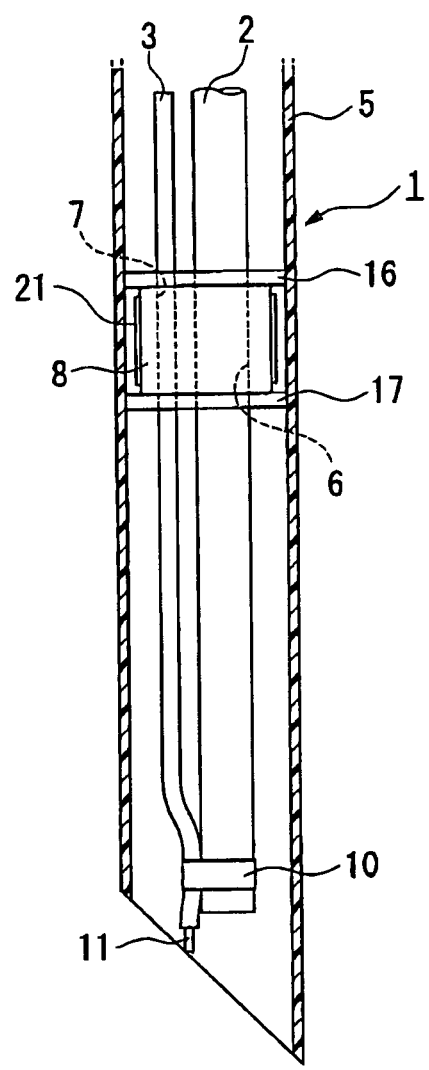
FIG. 2 is a partial cross sectional view of the insertion auxiliary implement, including partial side view of the endoscope insertion part and the ligation apparatus.
Figure 3:
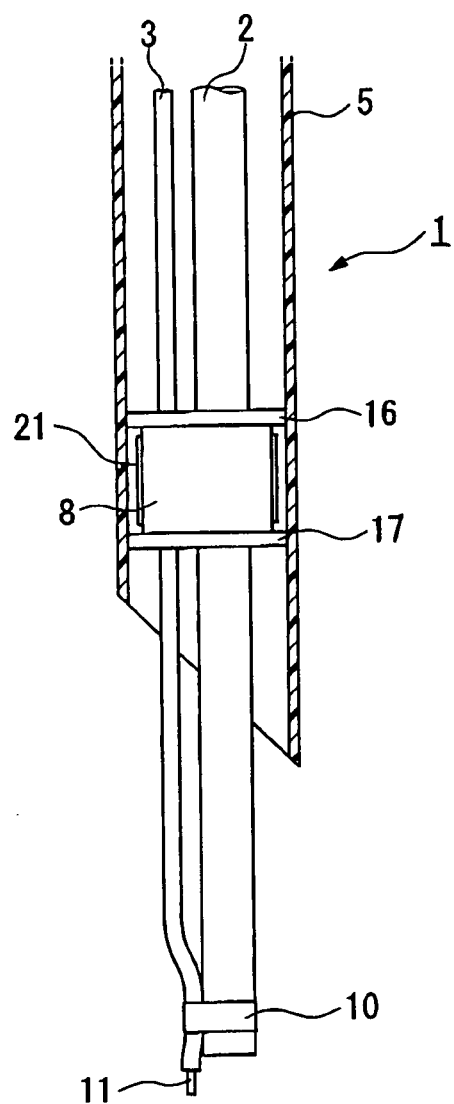
FIG. 3 is a partial cross sectional view of the insertion auxiliary implement, including partial side view of the endoscope insertion part and the ligation apparatus.

As shown in FIGS. 1 to 3, an insertion auxiliary implement 1 of the present invention includes: a tubular part 5 in which a flexible endoscope insertion part 2 which is inserted in a body cavity, and an external channel (channel) 3 are inserted; a sealing member 8 which has through holes 6 and 7 for supporting the endoscope insertion part 2 and the external channel 3 within the tubular part 5, and which airtightly and movably contacts each of a periphery of the endoscope insertion part 2, a periphery of the external channel 3, and an inner surface of the tubular part 5, and thereby maintains airtightness between a distal end and a proximal end inside the tubular part 5; and a fastener 10 which fastens the sealing member 8, the endoscope insertion part 2, and the external channel 3 together, after inserting the endoscope insertion part 2 and the external channel 3 into the sealing member 8.

As shown in FIG. 1, the external channel 3 is provided with: an insertion port 12 in which a ligation apparatus (treatment tool) 11 can be inserted; and a flexible main body 13 which covers the ligation apparatus 11 so that the ligation apparatus 11 can be inserted therein, and which is arranged along the endoscope insertion part 2. An O-ring (sealing structure) 15 is arranged within the insertion port 12, and the O-ring 15 can airtightly contact the periphery of the ligation apparatus 11.

As shown in FIGS. 1 to 3, the tubular part 5 is formed so that it has a length of 1 m, or preferably of 600 mm, which is necessary for reaching the stomach through the mouth, and so that the tubular part 5 has flexibility. In addition, a distal end of the tubular part 5 is bent in a slanted direction toward a distal end of the endoscope insertion part 5 so that it can be easily inserted into the body cavity. However, it is also possible to adopt a configuration in which the tubular part 5 is not bent in a slanted direction. Furthermore, the proximal end inside the tubular part 5 is formed so that the opening area thereof expands towards the proximal end direction so that the endoscope insertion part 2 can be easily inserted.

Figure 4:
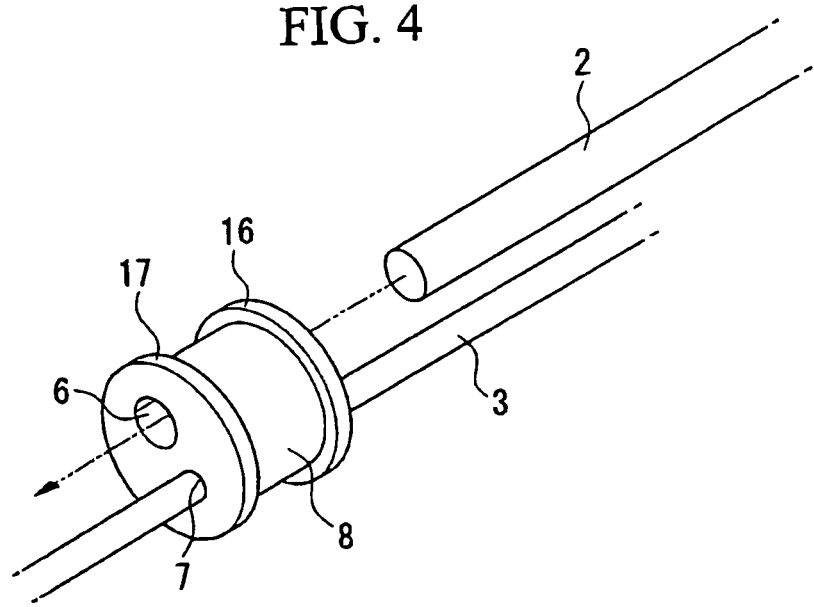
FIG. 4 is a perspective view of a sealing member, etc., of the insertion auxiliary implement.

As shown in FIG. 4, the sealing member 8 is substantially formed in a rod shape. Furthermore, within the sealing member 8, through holes 6 and 7 are formed so that their inner shapes fit the cross sectional shapes of the endoscope insertion part 2 and the external channel 3, and further so that they are arranged along the axial direction of the sealing member 8. The sealing member 8 of the present invention adopts ethylene-propylene rubber as one example of the material; however, other elastic materials having elasticity such as natural rubber, isoprene rubber, chloroprene rubber, silicone rubber, fluorocarbon rubber, SEBS rubber, and SIBS rubber can be adopted.

The sealing member 8 is formed so that the outer diameter at a middle portion in its axial direction is smaller than the inner diameter of the tubular part 5, and thereby a gap is formed between the middle portion and the inner surface of the tubular part 5. On the other hand, convexities (first slide portion) 16 and 17 which have external shapes which fit with the internal shape of the tubular part 5 by protruding radially and outwardly in convex shapes, and thereby airtightly and slidably contact the inner surface of the tubular part 5, are each provided at two ends in the axial direction of the periphery of the sealing member 8. These convexities 16 and 17 have elasticity and outer diameters larger than an inner diameter of the tubular part 5.

Figure 5:
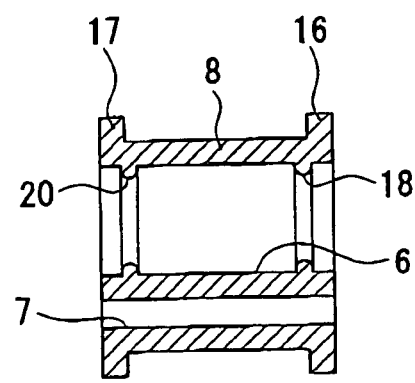
FIG. 5 is a cross sectional view of the sealing member of the insertion auxiliary implement, when it is seen in a section including its axis.

As shown in FIG. 5, flange-shaped convexities (second slide portion) 18 and 20 which protrude radially and inwardly in the diameter direction, and thereby airtightly and slidably contact the periphery of the endoscope insertion part 2, are formed at two ends of the through hole 6 along its axial direction. These convexities 18 and 20 have elasticity and inner diameter smaller than an outer diameter of the endoscope tubular part 2.

Figure 6A:
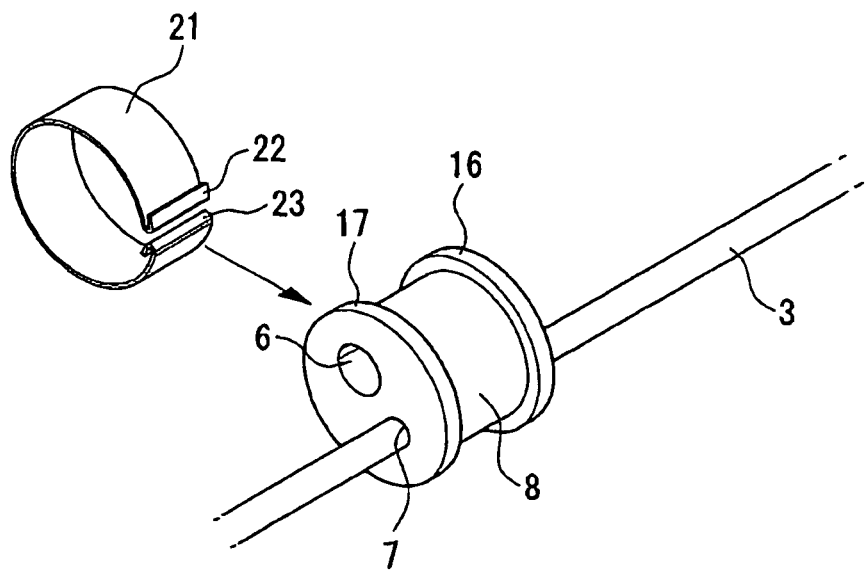
FIG. 6A is a perspective view of an reinforcing band, etc., of the insertion auxiliary implement.

As shown in FIG. 6A, the sealing member 8 has a reinforcing band 21 which wraps around the sealing member 8 so that it covers a peripheral portion between the convexities 16 and 17 of the sealing member 8.

Figure 6B:
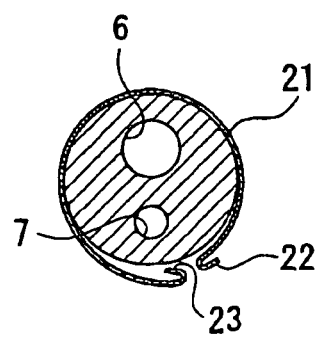
FIGS. 6B and 6C are cross sectional views of the reinforcing band, etc., when they are seen in a section perpendicular to the axis.
Figure 6C:
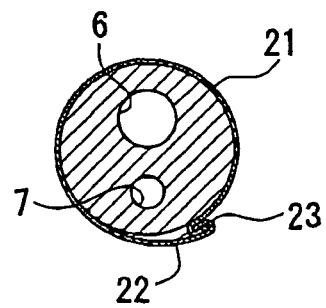

The reinforcing band 21 is made by bending a metal plate so that it forms a cylindrical shape having an inner diameter which is substantially the same as an outer diameter of a middle portion of the sealing member 8 in the axial direction. In the case in which the reinforcing band 21 is made of metal, stainless steel is preferable as the material; however, other materials such as steel, aluminum, copper, titanium, and other alloys may be employed. In the case in which the reinforcing band 21 is made of resin, polyether etherketone, acrylonitrile butadiene styrene resin, polycarbonate, polypropylene, liquid crystal polymer, POM, polysulfone, polyphenylsulphone, high density polyethylene, low density polyethylene, acrylic resin, etc., may be employed. A folded portion 22 which is folded outwardly in the diameter direction of the reinforcing band 21, and a folded portion 23 which is folded inwardly in the diameter direction of the reinforcing band 21, are formed at two ends of the reinforcing band 21 in the circular direction. As shown in FIGS. 6B and 6C, the folded portion 22 at one end and the folded portion 23 at another end are able to engage each other.

Figure 12:
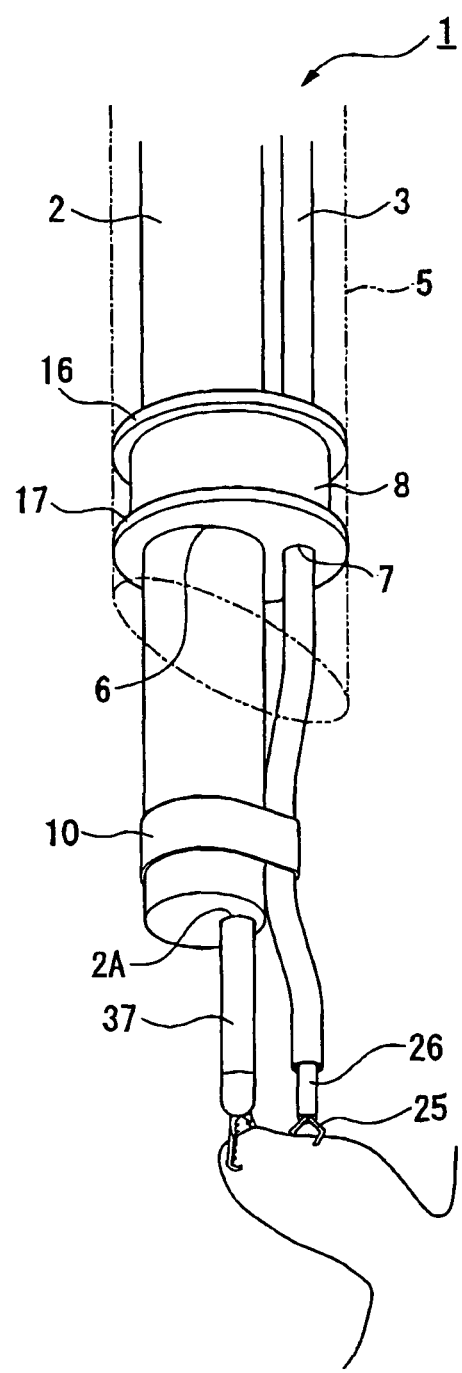
FIG. 12 is a diagram for explanation of use of the insertion auxiliary implement.

As shown in FIGS. 1 and 12, the ligation apparatus 11 has: a clip 25 which is provided at the distal end, and which can clamp and ligate a living tissue; an elastic guide tube 26 in which the clip 25 can be inserted; and a control part 27 for operating a ligation using the clip 25.

Figure 7:
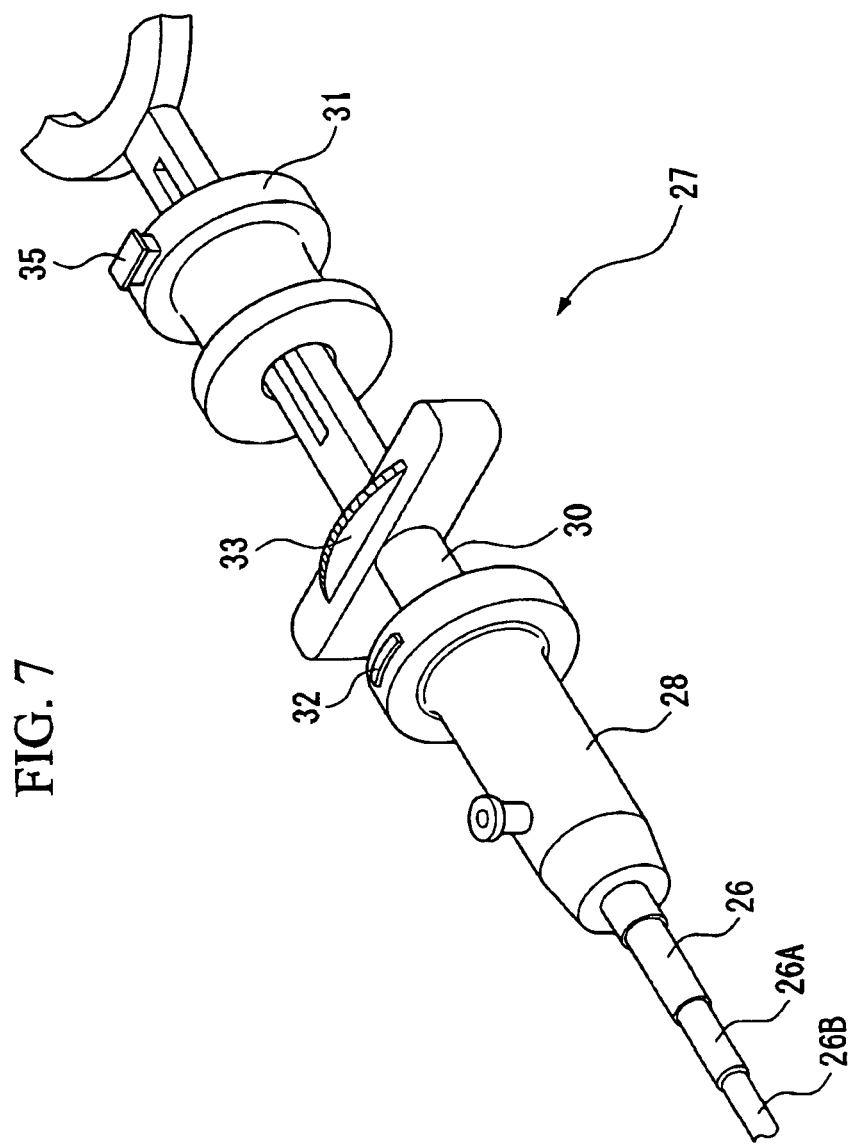
FIG. 7 is a perspective view of a control pan of the ligation apparatus which is used together with the insertion auxiliary implement.

As shown in FIG. 7, the control part 27 includes: a control part main body 28; a first slider 30 which is attached to the control part main body 28 so that it freely slides along an axial direction of the control part main body 28; and a second slider 31 which is attached, via a ratchet mechanism (not shown in the figures), to the first slider 30 so that it freely slides along the above-mentioned axial direction.

A control tube 26A connected to the first slider 30 at proximal end thereof and a control wire 26B connected to the second slider 31 at proximal end thereof, are provided in the guide tube 26 so that a relative movement is possible.

The control part main body 28 includes a first button 32 which fixes the first slider 30 with respect to the control part main body 28, and releases the fixation of the first slider 30 when the first button 32 is pressed. In addition, the first slider 30 includes a dial 33 for operating rotation of the clip 25 which is provided at the distal end side. Furthermore, a second button 35 which allows insertion and extraction of the second slider 31 with respect to the first slider 30 when the second button 35 is pressed, while fixes the second slider 31 at its position when the second button 35 is released.

Each component of the control part 27 is distinguished by colors, for example, red for the first button 32, yellow for the control part main body 28, white for the first slider 30, black for the dial 33, yellow for the second slider 31, and orange for the second button 35.

Next, use, functions, and benefits of the insertion auxiliary implement 1 according to the present embodiment will be explained.

Figure 8:
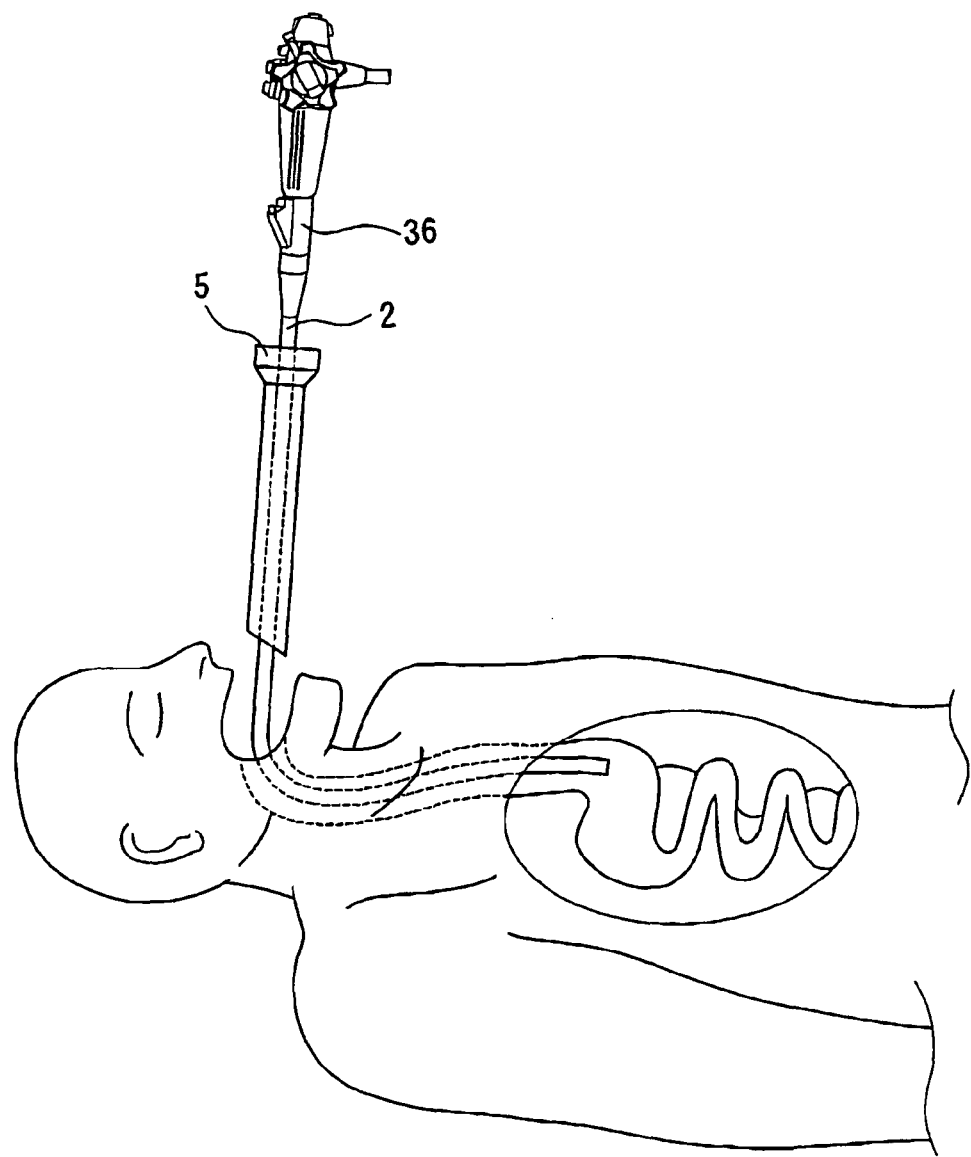
FIG. 8 is a diagram for explanation of use of the insertion auxiliary implement.

Firstly, as shown in FIG. 8, the endoscope insertion part 2 is inserted into the tubular part 5, and then is passed through the tubular part 5. Thereafter, only the endoscope insertion part 2 is inserted into the stomach through the mouth.

Then, the tubular part 5 is inserted from the distal end side into the mouth of the patient using the endoscope insertion part 2 as a guide for the insertion. Then, the tubular part 5 is inserted until the distal end reaches inside the stomach via the esophagus.

Figure 9:
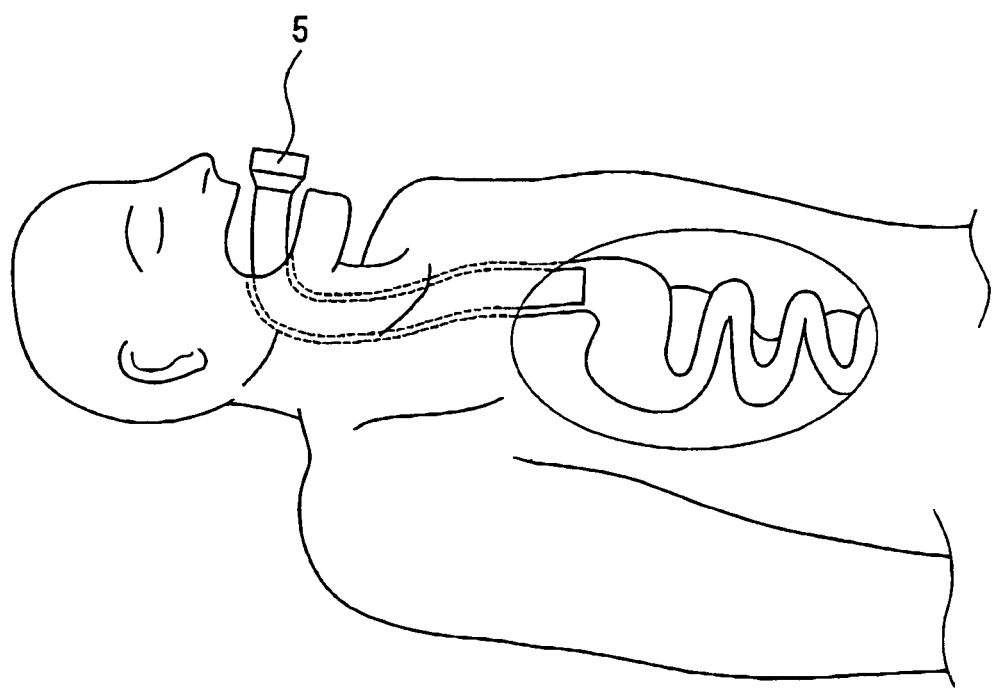
FIG. 9 is a diagram for explanation of use of the insertion auxiliary implement.

Thereafter, by extracting only the endoscope insertion tube 2 out of the body, the state will be as shown in FIG. 9.

Next, as shown in FIG. 4, the endoscope insertion part 2 is inserted into the through hole 6 of the sealing member 8, and the external channel 3 is inserted into the through hole 7 of the sealing member 8. At this time, if necessary, by applying a lubricant such as silicone oil on the peripheries of the endoscope insertion part 2 and the external channel 3 in advance, these endoscope insertion part 2 and external channel 3 can be smoothly inserted into the through holes 6 and 7.

The sealing member 8 is arranged at about 600 mm away from the proximal end of the endoscope insertion part 2. Then, the reinforcing band 21 wraps around the periphery between the convexities 16 and 17 of the sealing member 8, and then the folded portion 22 is fixed to the folded portion 23 by engaging it with the folded portion 23. Thereafter, the ligation apparatus 11 is inserted into the external channel 3, and then the distal end side of the endoscope insertion part 2 and the distal end side of the external channel 3 are fastened by the fastener 10.

Figure 10:
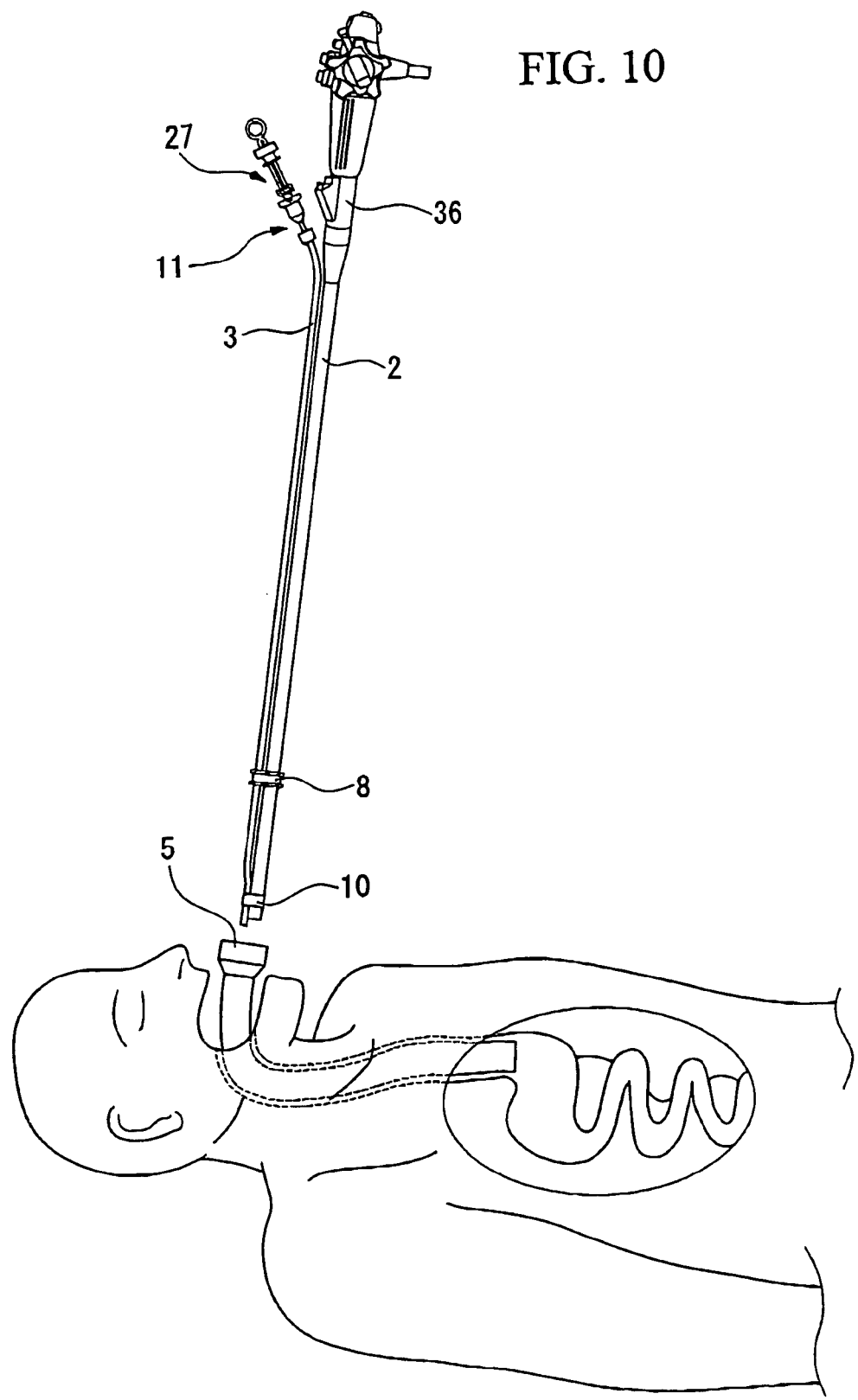
FIG. 10 is a diagram for explanation of use of the insertion auxiliary implement.
Figure 11:
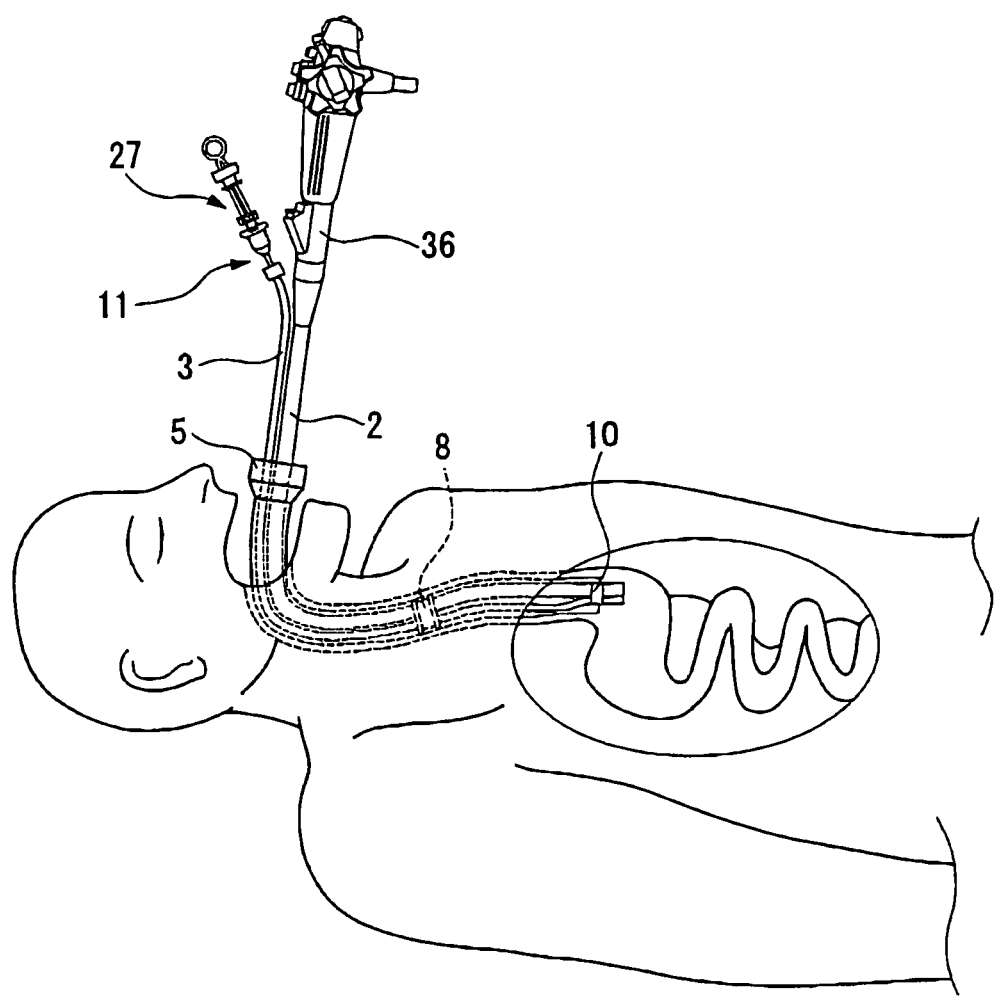
FIG. 11 is a diagram for explanation of use of the insertion auxiliary implement.

As shown in FIG. 10, the endoscope insertion part 2 equipped with the ligation apparatus 11 via the external channel 3, is inserted with the sealing member 8 into the tubular part 5. At this time, if necessary, by applying a lubricant such as silicone oil on the peripheries of the endoscope insertion part 2, the external channel 3, and the sealing member 8 in advance, these can be smoothly inserted into the tubular part 5. Next, as shown in FIG. 11, the distal end of the endoscope insertion part 2 is protruded outwardly from the distal end of the tubular part 5. At this time, since each of the endoscope insertion part 2, the external channel 3, and the guide tube 26 of the ligation apparatus 11 has flexibility, it is possible to bend an endoscope control part 36 and the control part 27 protruded from the proximal end side of the tubular part 5, so that they can easily be operated by an operator, if necessary.

Then, as shown in FIG. 12, predetermined treatments are performed at predetermined locations. At this time, if necessary, another treatment tool (for example, clamp forceps 37 which is also shown in the FIG. 12) is inserted into a forceps channel 2A in advance.

Next, in order to secure a space for treatments, air is supplied into the stomach through the endoscope insertion part 2 using an air supplier (which is not shown in the figures) so as to distends the stomach. At this time, the convexities 18 and 20 of the through hole 6, and the endoscope insertion part 2 airtightly and movably contact with each other; the through hole 7 and the external channel 3 airtightly and movably contact with each other; the tubular part 5, and the convexities 16 and 17 airtightly and movably contact with each other, the guide tube 26 of the ligation apparatus 11 and the O-ring 15 airtightly and movably contact with each other. Therefore, it is possible to decrease the possibility of a connection between the body cavity and the exterior of the body cavity through the tubular part 5. Therefore, it is possible to distend the stomach without leakage of air supplied within the stomach. As the result, it is possible to reliably secure the space for treatments within the stomach.

Then, near a treatment part, the treatments will be performed by forwarding and extracting the endoscope insertion part 2, the clamp forceps 37, and the ligation apparatus 11 with respect to the tubular part 5, or by forwarding and extracting the sealing member 8 with respect to the tubular part 5, if necessary. Also at this time, since the airtightness inside the stomach is held by the sealing member 8, in the same way as above, it is possible to decrease the possibility of a connection between the body cavity and the exterior of the body cavity through the tubular part 5. Therefore, the stomach is held in a distended state.

A ligation treatment will be performed in this state.

Operations, etc., of the ligation apparatus 11 will be performed by following instructions from another operator who does not operate the endoscope insertion part 2. Meanwhile, the operator is required to perform a variety of operations in a short time and reliably. In the present embodiment, each of the first button 32, the control part main body 28, the first slider 30, the dial 33, the second slider 31, and the second button 35 of the control part 27 are distinguished by colors. Therefore, by understanding, in advance, the relationships between the colors and each part to be operated, it becomes possible to simply instruct an order and the use of the control part 27 to the operator of the control part 27, by calling out their colors.

Moreover, the same benefits can be obtained by applying numbers, etc., which indicate the order of operations instead of the colors.

According to the above-mentioned insertion auxiliary implement 1 of the present embodiment, it is possible to decrease the possibility of a connection between the body cavity and the exterior of the body cavity through the tubular part 5 when the endoscope insertion part 2 and the external channel 3 are supported in the tubular part 5 by the sealing member 8. Therefore, it is possible to perform insertion and extraction of the sealing member 8 with respect to the tubular part 5, while maintaining the airtightness between the inner surface of the tubular part 5 and the periphery of the sealing member 8. Identically, insertion and extraction of the endoscope insertion part 2 and the external channel 3 with respect to the sealing member 8 also can be performed.

At this time, since the sealing member 8 airtightly contacts the inner surface of the tubular part 5 at the convexities 16 and 17, contact areas between the sealing member 8 and the tubular part 5 become smaller than a total area of an outer surface of the sealing member 8; thereby, a friction resistance therebetween can be smaller. Therefore, the sealing member 8 can be easily inserted into and extracted from the tubular part 5.

Similarly, since the sealing member 8 airtightly contacts the endoscope insertion part 2 at the convexities 18 and 20, contact areas between the sealing member 8 and the endoscope insertion part 2 become smaller than the total area of an inner surface of the through hole 6; thereby a friction resistance therebetween can be smaller. Therefore, the endoscope insertion part 2 can be easily inserted and extracted with respect to the sealing member 8.

In addition, by the wrapping around the sealing member 8 by the reinforcing band 21 so that the peripheral portion between the convexities 16 and 17 of the sealing member 8 is covered, it becomes possible to decrease the possibility of twisting and deforming the sealing member 8 (especially the convexities 16 and 17) when inserting and extracting the sealing member 8 in the tubular part 8. Therefore, it is possible to maintain the airtightness between the tubular part 5 and the endoscope insertion part 2, and the airtightness between the tubular part 5 and the external channel 3, in good condition.

Furthermore, by fastening the endoscope insertion part 2 and the external channel 3 by the fastener 10, it becomes possible to fasten the endoscope insertion part 2 and the external channel 3 more strongly than in the case of using the sealing member 8 without the fastener 10. Therefore, it is possible to perform stable insertion and extraction of the endoscope insertion part 2 and the external channel 3 in the tubular part 5.

Furthermore, even in the case in which repetition of insertion and extraction of the ligation apparatus 11 is required, since the ligation apparatus 11 can be inserted and extracted within the external channel 3 while the external channel 3 is fixed to the tubular part 5, it is possible to maintain the airtightness between the external channel 3 and the sealing member 8 in a good condition.

Next, a second embodiment of the present invention will be explained with reference to FIGS. 13 and 14.

Moreover, in the following explanation, the same reference numerals will be used for the same components explained in the above-mentioned first embodiment.

An insertion auxiliary implement 38 according to the present embodiment differs from the insertion auxiliary implement 1 according to the above-mentioned first embodiment in the points in which: a sealing member 40 is fixed to the inner surface at the proximal end side of the tubular part 5; the ligation apparatus 11 is directly held by the sealing member 40 without the external channel 3; and a slit 40A is provided between the through holes 41 and 6.

The through hole 41 has an internal shape which fits with the outer shape of the guide tube 26 of the ligation apparatus 11 when they are seen in the cross sectional view which is vertical to an axis of the guide tube 26, thereby the through hole 41 can support the guide tube 26. In addition, as shown in FIG. 14, convexities (third slide portion) 42 and 43 which protrude inwardly in the diameter direction, and thereby airtightly and slidably contact the periphery of the guide tube 26, are formed at two ends of the through hole 41 along its axial direction. These convexities 42 and 43 have elasticity and inner diameters smaller than an outer diameter of the guide tube 26. Identically, convexities 18 and 20 are arranged at two ends of the through hole 6. Therefore, each of the periphery of the guide tube 26 and the periphery of the endoscope insertion part 2 airtightly and movably contacts the sealing member 40. Accordingly, airtightness between the distal end and the proximal end inside the tubular part 5 is maintained. Furthermore, after the endoscope insertion part 2 and the guide tube 26 are inserted within the sealing member 40, the fastener 10 fastens these endoscope insertion part 2 and the guide tube 26 with each other.

Next, use, functions, and benefits of the insertion auxiliary implement 38 according to the present embodiment will be explained.

Firstly, as in the above-mentioned first embodiment, the tubular part 5 is inserted from the distal end side into the mouth of the patient, and is further inserted until the distal end reaches inside the stomach via the esophagus.

After the endoscope insertion part 2 and the guide tube 26 are fastened by the fastener 10, these endoscope insertion part 2 and guide tube 26 are inserted into the tubular part 5.

After the insertion, as in the above-mentioned first embodiment, the stomach is distended by supplying air into the stomach through the endoscope insertion part 2.

At this time, the convexities 18 and 20 of the through hole 6, and the endoscope insertion part 2 airtightly and movably contacts with each other, the convexities 42 and 43 of the through hole 41, and the guide tube 26 of the ligation apparatus 11 airtightly and movably contacts with each other. Therefore, it is possible to decrease the possibility of a connection between the body cavity and the exterior of the body cavity through the tubular part 5. Therefore, it is possible to distend the stomach without leakage of air supplied within the stomach.

Thereafter, predetermined treatments using the ligation apparatus 11, etc., will be performed.

According to the insertion auxiliary implement 38 of the above-mentioned embodiment, the same functions and benefits as the insertion auxiliary implement 1 according to the first embodiment will be obtained. Furthermore, since the sealing member 40 is fixed to the tubular part 5, a space between the inner surface of the tubular part 5 and the periphery of the sealing member 40 are reliably sealed; thereby the airtightness between the distal end and the proximal end inside the tubular part 5 can be maintained in better condition.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, in each of the above-mentioned embodiments, the endoscope insertion part 2 and the external channel 3 airtightly and movably contact the sealing member 8, the endoscope insertion part 2 and the ligation apparatus 11 of the guide tube 26 airtightly and movably contact the sealing member 40, the sealing member 8 airtightly and movably contact the tubular part 5; however, at least one of these may be fixed to the sealing member 8 or the sealing member 40.

Furthermore, in the first embodiment, the ligation apparatus 11 may be inserted through the sealing member 8 without using the external channel 3, by forming the shape of the through hole 7 of the sealing member 8 so that it fits with the external shape of the guide tube 26, and airtightly and movably contacting the guide tube 26 to the through hole 7.

Figure 15A:
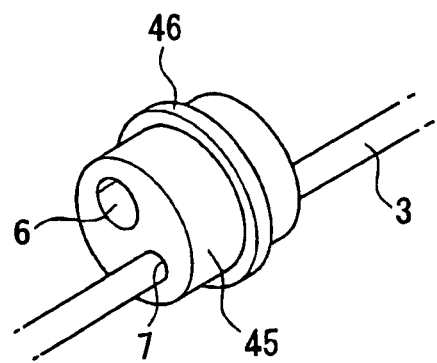
FIGS. 15A and 15B are perspective views of sealing member of an insertion auxiliary implement according to other embodiments of the present invention.
Figure 15B:
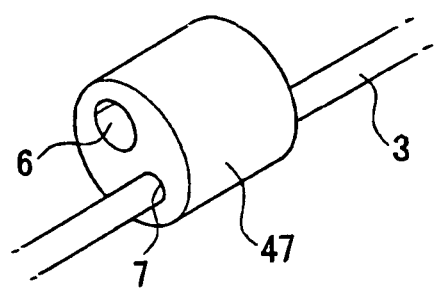

Furthermore, the convexities 16 and 17 are provided at two ends on the periphery of the sealing member 8 in the axial direction; however, the same functions and benefits can be obtained even in the case in which, as shown in FIG. 15A, single convexity 46 is provided at the middle portion in the axial direction on a periphery of a sealing member 45. Furthermore, as shown in FIG. 15B, another sealing member 47 which does not have convexities, and airtightly and slidably contacts the inner surface of the tubular part 5 at its whole external surface, may be employed. In this case, the friction resistance of the sealing member 41 with respect to the tubular part 5 increases in comparison with the above-mentioned first embodiment; however, in the point of maintaining airtightness, the same functions and the benefits can be obtained.

Shapes of the slide portions are not limited to the shapes of the convexities 16, 17, 18, 20, 42, 43, and 46; and other shapes may be employed instead of them.

As explained above, an insertion auxiliary implement of the present invention includes: a tubular part into which a flexible endoscope insertion part which is insertable into a body cavity, and one of a treatment tool and a channel into which the treatment tool is insertable, are insertable; and a sealing member which has through holes for supporting the endoscope insertion part and one of the treatment tool and the channel in the tubular part, and which airtightly and movably contacts each of a periphery of the endoscope insertion part, a periphery of the treatment tool or a periphery of the channel, and an inner surface of the tubular part, and thereby maintains airtightness between a distal end and a proximal end inside the tubular part.

Another insertion auxiliary implement of the present invention includes: a tubular part into which a flexible endoscope insertion part which is insertable into a body cavity, and one of a treatment tool and a channel into which the treatment tool is insertable, are insertable; and a sealing member which has through holes for supporting the endoscope insertion part and one of the treatment tool and the channel in the tubular part, and which is fixed to at least one of a periphery of the endoscope insertion part, a periphery of the treatment tool or a periphery of the channel, and an inner surface of the tubular part, and which is airtightly and movably contacted with others, and thereby maintains airtightness between a distal end and a proximal end inside the tubular part.

According to the above-mentioned insertion auxiliary implement or the above-mentioned another insertion auxiliary implement, by forming the through holes so that their inner shapes fit the cross sectional shapes of the endoscope insertion part and treatment tool, and further by forming the sealing member so that its outer shape fits the inner shape of the tubular part, when supporting the endoscope insertion part and the treatment tool or the channel in the tubular part by the sealing member, it becomes possible to decrease the possibility of connection between the body cavity and the exterior of the body cavity through the tubular member.

Therefore, according to the above-mentioned insertion auxiliary implement or the above-mentioned other insertion auxiliary implement of the present invention, it becomes possible to perform insertion and extraction operations of the endoscope insertion part and the treatment tool or the channel through the tubular part, while maintaining the airtightness between the distal end and the proximal end inside the tubular part. Therefore, since the predetermined treatment can be reliably performed in a short time, it becomes possible to decrease the burdens on an operator and on a patient.

The sealing member may include at least one of: a first slide portion which airtightly and slidably contacts the inner surface of the tubular part; a second slide portion which airtightly and slidably contacts the periphery of the endoscope insertion part; and a third slide portion which airtightly and slidably contacts the periphery of the treatment tool or the periphery of the channel.

In this case, it becomes possible to perform insertion and extraction of the sealing member with respect to the tubular part, while maintaining the airtightness between the tubular part and the sealing member. Otherwise, it becomes possible to perform insertion and extraction of the endoscope insertion part while maintaining the airtightness between the endoscope insertion part and the sealing member. Otherwise, it becomes possible to perform insertion and extraction of the treatment tool or the channel with respect to the sealing member, while maintaining the airtightness between the sealing member and the treatment tool or the channel.

The insertion auxiliary implement may satisfy at least one of the following: the first slide portion is a convexity which contacts the inner surface of the tubular part; the second slide portion is a convexity which contacts the periphery of the endoscope insertion part, and the third slide portion is a convexity which contacts the periphery of the treatment tool or the periphery of the channel.

In the case in which the sealing member airtightly contacts the inner surface of the tubular part at the convexity, since a contact area between the sealing member and the tubular part becomes smaller than a total area of an outer surface of the sealing member, a friction resistance therebetween can be smaller. Therefore, insertion and extraction operations of the sealing member can be performed easily.

Identically, in the case in which the sealing member airtightly contacts the endoscope insertion part and the treatment toot or the channel, since friction resistances can be smaller, insertion and extraction operations of the sealing member can be performed easily.

A reinforcing band may be provided which wraps around the sealing member so that an outer portion of the sealing member, which is away from the inner surface of the tubular part, is covered.

In this case, by the wrapping around the sealing member by the reinforcing band so that a portion where the convexity is not provided is covered, when inserting and extracting the sealing member within the tubular part, it becomes possible to decrease the possibility of twisting and thereby deforming the sealing member. Therefore, it becomes possible to maintain the airtightness of the periphery of the endoscope insertion part and the periphery of the treatment tool or the periphery of the channel, with respect to the sealing member in a good condition.

A fastener which fastens the endoscope insertion part, and one of the treatment tool and the channel together, may be provided.

In this case, by fastening the endoscope insertion part with the treatment tool or the channel by the fastener, it becomes possible to fasten both of them more strongly than in the case of using the sealing member without the fastener. Therefore, it is possible to perform stable insertion and extraction operations of the sealing member within the tubular part.

The channel in which the treatment tool is inserted may be inserted in the through hole of the sealing member, and a sealing structure may be provided between the inner surface of the channel and the periphery of the treatment tool.

In this case, even in the case in which repetition of insertion and extraction operations of the treatment tool is required, since the treatment tool can be inserted and extracted within the channel while the channel is fixed to the tubular part, it is possible to maintain the airtightness between the channel and the sealing member in a good condition.

What is claimed is:

1. An insertion auxiliary implement of a treatment tool, the insertion auxiliary implement apparatus comprising:
   a tubular part into which a flexible endoscope insertion part which is insertable into a body cavity, and one of a treatment tool and a channel into which the treatment tool is insertable, are inserted; and
   a sealing member which has through holes for supporting the endoscope insertion part and one of the treatment tool and the channel in the tubular part, wherein;
   the sealing member is adapted to be fixed to at least one of a periphery of the endoscope insertion part, a periphery of the treatment tool or a periphery of the channel; and
   at least one of the endoscope insertion part, the treatment tool, and the channel is slidable inside the tubular part; and
   the sealing member airtightly and movably contacts an inner surface of the tubular part for movement between a proximal end and a distal end inside the tubular part, and thereby maintains airtightness between the distal end and the proximal end inside the tubular part.

2. The insertion auxiliary implement according to claim 1, wherein
   the sealing member comprises a first slide portion which hermetically and slidably contacts the inner peripheral surface of the tubular part.

3. The insertion auxiliary implement according to claim 2, wherein the sealing member further comprises at least one of:
   a second slide portion which hermetically and slidably contacts the periphery of the endoscope insertion part; and
   a third slide portion which airtightly and slidably contacts the periphery of the treatment tool or the periphery of the channel of the first slide portion.

4. The insertion auxiliary implement according to claim 3, wherein at least one of:
   the first slide portion which contacts the inner surface of the tubular part, the second slide portion which contacts the periphery of the endoscope insertion part, and the third slide portion which contacts the periphery of the treatment tool or the periphery of the channel, comprises a protrusion having a convex shape.

5. The insertion auxiliary implement according to claim 1, further comprising a reinforcing band which wraps around the sealing member so that an outer portion of the sealing member, which is radially offset from the inner surface of the tubular part, is covered.

6. The insertion auxiliary implement according to claim 5, wherein the reinforcing band is non-contacting with the inner surface of the tubular part when the sealing member is inserted in the tubular part.

7. The insertion auxiliary implement according to claim 1, wherein the sealing member comprises two first slide portions which airtightly and slidably contact the inner peripheral surface of the tubular part, at at least two locations along an axial direction of the tubular part.

8. The insertion auxiliary implement according to claim 1, wherein:
   the sealing member comprises two second slide portions which airtightly and slidably contact the peripheral of the endoscope insertion part, at least two locations along an axial direction of the tubular part; and
   the sealing member comprises two third slide portions which hermetically and slidably contact the periphery of the treatment tool or the periphery of the channel, at at least two locations along an axial direction of the tubular part.

9. The insertion auxiliary implement according to claim 4, wherein:
   in the case in which the first slide portion comprises a first protrusion having a convex shape, the first protrusion has elasticity and external dimensions larger than internal dimensions of the tubular part;
   in the case in which the second slide portion comprises a second protrusion having a convex shape, the second protrusion has elasticity and internal dimensions smaller than external dimensions of the periphery of the endoscope insertion part; and
   in the case in which the second slide portion comprises a third protrusion having a convex shape, the third protrusion has elasticity and internal dimensions smaller than external dimensions of the periphery of the treatment tool or the periphery of the channel.

* * * * *